(12) United States Patent
Stetson

(10) Patent No.: US 8,983,800 B2
(45) Date of Patent: Mar. 17, 2015

(54) SELECTION OF PRESET FILTER PARAMETERS BASED ON SIGNAL QUALITY

(75) Inventor: Paul F. Stetson, Oakland, CA (US)

(73) Assignee: Covidien LP, Mansfield, MA (US)

( * ) Notice: Subject to any disclaimer, the term of this patent is extended or adjusted under 35 U.S.C. 154(b) by 2039 days.

(21) Appl. No.: 11/247,427

(22) Filed: Oct. 11, 2005

(65) Prior Publication Data
US 2006/0030766 A1    Feb. 9, 2006

Related U.S. Application Data

(63) Continuation of application No. 10/341,722, filed on Jan. 13, 2003, now Pat. No. 7,016,715.

(51) Int. Cl.
*A61B 5/00* (2006.01)
*A61B 5/1455* (2006.01)
*G06K 9/00* (2006.01)
*A61B 5/01* (2006.01)
*A61B 5/021* (2006.01)
*A61B 5/024* (2006.01)

(52) U.S. Cl.
CPC ............. *A61B 5/14551* (2013.01); *A61B 5/725* (2013.01); *G06K 9/00503* (2013.01); *A61B 5/7221* (2013.01); *A61B 5/01* (2013.01); *A61B 5/021* (2013.01); *A61B 5/02416* (2013.01); *A61B 5/7203* (2013.01); *A61B 5/7239* (2013.01)
USPC .......................................... 702/191; 600/323

(58) Field of Classification Search
USPC ........................................................ 702/190
See application file for complete search history.

(56) References Cited

U.S. PATENT DOCUMENTS

| 3,638,640 | A | | 2/1972 | Shaw |
|---|---|---|---|---|
| 4,714,341 | A | | 12/1987 | Hamaguri et al. |
| 4,805,623 | A | | 2/1989 | Jöbsis |
| 4,807,631 | A | | 2/1989 | Hersh et al. |
| 4,833,714 | A | * | 5/1989 | Shimotani et al. ............ 704/253 |
| 4,911,167 | A | | 3/1990 | Corenman et al. |
| 4,913,150 | A | | 4/1990 | Cheung et al. |
| 4,936,679 | A | | 6/1990 | Mersch |
| 4,938,218 | A | | 7/1990 | Goodman et al. |
| 4,971,062 | A | | 11/1990 | Hasebe et al. |
| 4,972,331 | A | | 11/1990 | Chance |

(Continued)

FOREIGN PATENT DOCUMENTS

| DE | 19640807 | 9/1997 |
|---|---|---|
| EP | 1491135 | 12/2004 |

(Continued)

OTHER PUBLICATIONS

Wirnitzer, Bernhard, Adaptive Filters, A Matlab (Nano) Toolbox and Laboratory Exercises, ver. 1.0 Oct. 99, FH-Mannheim—Institut fur Digitale Signalverabeitung.

(Continued)

*Primary Examiner* — Manuel L Barbee
(74) *Attorney, Agent, or Firm* — Fletcher Yoder, P.C.

(57) ABSTRACT

Methods and devices for reducing noise effects in a system for measuring a physiological parameter, including receiving an input signal, obtaining an assessment of the signal quality of the input signal, selecting coefficients for a digital filter using the assessment of signal quality; and filtering the input signal using the digital filter, without comparing the filter's output signal with the input signal.

28 Claims, 2 Drawing Sheets

(56) References Cited

U.S. PATENT DOCUMENTS

| | | | |
|---|---|---|---|
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,357,965 A * | 10/1994 | Hall et al. | 600/454 |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,506,798 A | 4/1996 | Shimada et al. | |
| 5,553,614 A | 9/1996 | Chance | |
| 5,564,417 A | 10/1996 | Chance | |
| 5,575,285 A | 11/1996 | Takanashi et al. | |
| 5,594,807 A * | 1/1997 | Liu | 382/128 |
| 5,611,337 A | 3/1997 | Bukta | |
| 5,630,413 A | 5/1997 | Thomas et al. | |
| 5,632,272 A * | 5/1997 | Diab et al. | 600/323 |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Kuenstner | |
| 5,730,124 A | 3/1998 | Yamauchi | |
| 5,758,644 A | 6/1998 | Diab et al. | |
| 5,769,785 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,052,659 A * | 4/2000 | Mermelstein | 704/219 |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,135,952 A | 10/2000 | Coetzee | |
| 6,142,942 A | 11/2000 | Clark | |
| 6,150,951 A | 11/2000 | Olejniczak | |
| 6,154,667 A | 11/2000 | Miura et al. | |
| 6,157,850 A | 12/2000 | Diab et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,631,281 B1 | 10/2003 | Kastle | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,836,235 B2 * | 12/2004 | Asami | 341/155 |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,006,856 B2 | 2/2006 | Baker, Jr. et al. | |
| 7,016,715 B2 | 3/2006 | Stetson | |
| 7,024,235 B2 | 4/2006 | Melker et al. | |
| 7,027,849 B2 | 4/2006 | Al-Ali | |
| 7,027,850 B2 | 4/2006 | Wasserman | |
| 7,030,749 B2 | 4/2006 | Al-Ali | |
| 7,035,697 B1 | 4/2006 | Brown | |
| 7,047,056 B2 | 5/2006 | Hannula et al. | |
| 7,060,035 B2 | 6/2006 | Wasserman | |
| 7,110,951 B1 * | 9/2006 | Lemelson et al. | 704/270 |
| 7,127,278 B2 | 10/2006 | Melker et al. | |
| 7,162,306 B2 | 1/2007 | Caby et al. | |
| 7,209,775 B2 | 4/2007 | Bae et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,373,193 B2 | 5/2008 | Al-Ali et al. | |
| 7,392,075 B2 | 6/2008 | Baker, Jr. | |
| 7,474,907 B2 | 1/2009 | Baker, Jr. | |
| 7,496,393 B2 | 2/2009 | Diab et al. | |
| 7,519,488 B2 | 4/2009 | Fu et al. | |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |

(56) References Cited

U.S. PATENT DOCUMENTS

| | | |
|---|---|---|
| 2002/0003832 A1 | 1/2002 | Siefert |
| 2002/0026106 A1 | 2/2002 | Khalil et al. |
| 2002/0034222 A1* | 3/2002 | Buchwald et al. ............ 375/232 |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0045806 A1* | 4/2002 | Baker et al. ................... 600/309 |
| 2002/0049389 A1 | 4/2002 | Abreu |
| 2002/0062071 A1 | 5/2002 | Diab et al. |
| 2002/0099282 A1 | 7/2002 | Knobbe et al. |
| 2002/0111748 A1 | 8/2002 | Kobayashi et al. |
| 2002/0128544 A1 | 9/2002 | Diab et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0043925 A1* | 3/2003 | Stopler et al. ................. 375/254 |
| 2003/0053617 A1 | 3/2003 | Diethorn |
| 2003/0055324 A1 | 3/2003 | Wasserman |
| 2003/0060693 A1 | 3/2003 | Monfre et al. |
| 2003/0069727 A1* | 4/2003 | Krasny et al. ................. 704/228 |
| 2003/0115061 A1* | 6/2003 | Chen .............................. 704/240 |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2003/0223489 A1 | 12/2003 | Smee et al. |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0138538 A1 | 7/2004 | Stetson |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0049468 A1 | 3/2005 | Carlson et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0197552 A1 | 9/2005 | Baker, Jr. et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0030766 A1 | 2/2006 | Stetson |
| 2006/0052680 A1 | 3/2006 | Diab |
| 2006/0058683 A1 | 3/2006 | Chance |
| 2006/0064024 A1 | 3/2006 | Schnall |
| 2006/0122476 A1 | 6/2006 | Van Slyke |
| 2006/0135860 A1 | 6/2006 | Baker, Jr. et al. |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2007/0073120 A1 | 3/2007 | Li et al. |
| 2007/0073124 A1 | 3/2007 | Li et al. |
| 2008/0255436 A1 | 10/2008 | Baker |

FOREIGN PATENT DOCUMENTS

| | | |
|---|---|---|
| JP | 3170866 | 7/1991 |
| JP | 3238813 | 10/1991 |
| JP | 4332536 | 11/1992 |
| JP | 7124138 | 5/1995 |
| JP | 7136150 | 5/1995 |
| JP | 10216115 | 8/1998 |
| JP | 2003210438 | 7/2003 |
| JP | 2003275192 | 9/2003 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |
| WO | WO9309711 | 5/1993 |
| WO | WO9316629 | 9/1993 |
| WO | WO9843071 | 10/1998 |
| WO | WO0021438 | 4/2000 |

OTHER PUBLICATIONS

Vincente, L.M., et al.; "Adaptive Pre-Processing of Photoplethysmographic Blood Volume Pulse Measurements," pp. 114-117 (1996).

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Todd, Bryan, et al.; "The Identification of Peaks in Physiological Signals," *Computers and Biomedical Research*, vol. 32, pp. 322-335 (1999).

A. Johansson; "Neural network for photoplethysmographic respiratory rate monitoring," *Medical & Biological Engineering & Computing*, vol. 41, pp. 242-248 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Canadian Office Action for Application No. 2,512,579 dated May 30, 2012; 4 pgs.

* cited by examiner

SELECTION OF PRESET FILTER PARAMETERS BASED ON SIGNAL QUALITY

CROSS-REFERENCE TO RELATED APPLICATIONS

This application is a Continuation of U.S. application Ser. No. 10/341,722, filed Jan. 13, 2003, now U.S. Pat. No. 7,016,715 the disclosure of which is hereby incorporated by reference.

BACKGROUND OF THE INVENTION

The present invention relates to the processing of signals obtained from a medical diagnostic apparatus, such as a pulse oximeter, using a digital filter to reduce noise effects.

A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING," issued Dec. 29, 1998, and U.S. Pat. No. 4,911,167, entitled "METHOD AND APPARATUS FOR DETECTING OPTICAL PULSES," issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. Most pulse oximeters extract the plethysmographic signal having first determined saturation or pulse rate, both of which are susceptible to interference.

A challenge in pulse oximetry is in analyzing the data to obtain a reliable measure of a physiologic parameter in the presence of large interference sources. Various solutions to this challenge have included methods that assess the quality of the measured parameter and decide on displaying the measured value when it is deemed reliable based upon a signal quality. Another approach involves a heuristic-based signal extraction technology, where the obtained signals are processed based on a series of guesses of the ratio, and which require the algorithm to start with a guess of the ratio, which is an unknown. Both the signal-quality determining and the heuristic signal extraction technologies are attempts at separating out a reliable signal from an unreliable one, one method being a phenomenological one and the other being a heuristic one.

A known approach for the reduction of noise in medical diagnostic devices including pulse oximeters involves the use of an adaptive filter, such as an adaptive digital filter. The adaptive filter is actually a data processing algorithm, and in most typical applications, the filter is a computer program that is executed by a central processor. As such, the filter inherently incorporates discrete-time measurement samples rather than continuous time inputs. A type of digital filter that is used in pulse oximeter systems is a Kalman filter. While conventional adaptive digital filters in general and Kalman filters in particular have been assimilated in medical diagnostics system to help reduce noise in a signal, there are still many challenges that need to be addressed to improve the techniques that are used to reduce noise effects in signals; noise effects such as those present in a medical diagnostic device. One of the shortcomings of using a Kalman filter is that a Kalman filter is an adaptive filter whose functioning is mathematically-based and where its aim is to compare the output of the filter with a desired output, and reduce the error in the comparison by continuously varying the filter's coefficients. So, a Kalman filter generates filter coefficients in an adaptive manner to minimize an error. While this method has been adopted by many, it is still a method that is somewhat blind regarding the signal that it is being filtered. Such an approach does not take into account the unique attributes that an input signal may possess and which are physiologically based. Another shortcoming of the Kalman filtering is that the Kalman filter is linear in its input-output relationship. One can appreciate that in certain conditions, the requirement that the filter be linear in its input-output relationship is too constraining. Yet another shortcoming of a Kalman filter is that filter parameters are continuously tuned, which can be computationally expensive.

There is therefore a need to develop a filter for reducing noise effects in signals that does not suffer form the above-mentioned constraints of conventional adaptive filters.

BRIEF SUMMARY OF THE INVENTION

The present invention is directed towards methods and devices for reducing noise effects in a system for measuring a physiological parameter, including receiving an input signal; obtaining an assessment of the signal quality of the input signal; selecting coefficients for a digital filter using the assessment of signal quality; and filtering the input signal using the digital filter, without comparing the filter's output signal with the input signal.

In certain aspects, the filter coefficients are selected from a plurality of discrete preset values. In certain embodiments, the discrete and preset values are fixed or non-changing values. The digital filter can have either a linear or preferably a non-linear input-output relationship.

In pulse oximetry applications, the quality of the input signal may be assessed by obtaining or measuring signal parameters that include the skew of the time derivative of the signal; the correlation between signals from different wavelengths; the variation in signal amplitude, as well as others. Other assessments, such as maximum values or spectral peak frequencies, may also be used in determining filter parameters.

In some embodiments, the selection of filter parameters or coefficients is performed in real time, with the coefficients of the digital filter being determined using a current input sample. In certain other embodiments, the selection of filter parameters is performed using a previously stored input signal sample.

In pulse oximetry applications, the input signals can be a function of an oxygen saturation, or a pulse rate. Furthermore, these signals correspond with sensed optical energies from a plurality of wavelengths.

For a further understanding of the nature and advantages of the invention, reference should be made to the following description taken in conjunction with the accompanying drawings.

DETAILED DESCRIPTION OF THE INVENTION

The methods and systems in accordance with embodiments of the present invention are directed towards selecting and adjusting the parameters of a digital filter based an assessment of the quality of the input signals to the filter. The invention is particularly applicable to and will be explained by reference to measurements of oxygen saturation of hemoglobin in arterial blood and patient heart rate, as in pulse oximeter monitors and pulse oximetry sensors. However, it should be realized the invention is equally applicable to any generalized patient monitor and associated patient sensor, such as ECG, blood pressure, temperature, etc., and is not to be limited for use only with oximetry or pulse oximetry.

Figure 1:
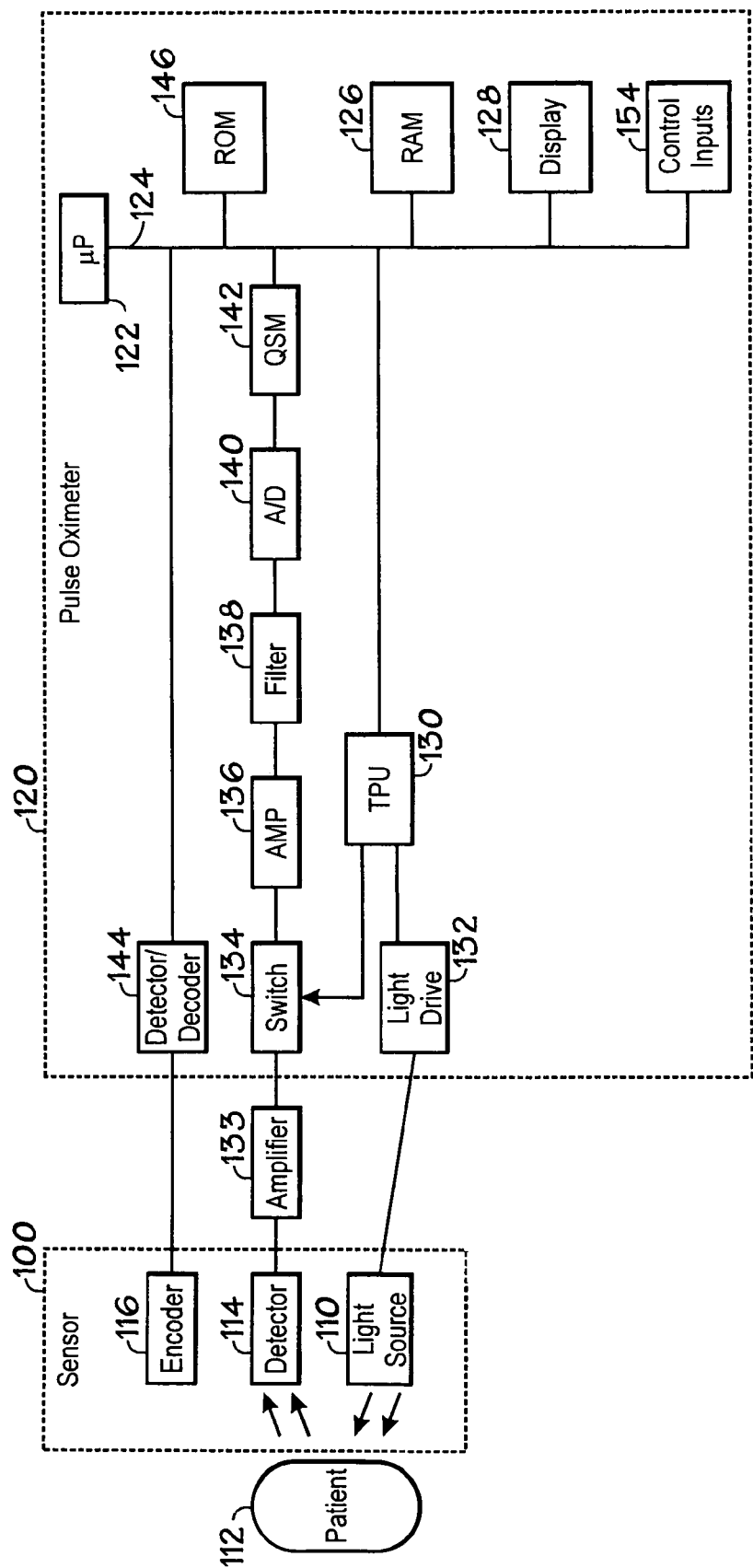
FIG. 1 is a block diagram of an exemplary oximeter.

FIG. 1 is a block diagram of one embodiment of a pulse oximeter that may be configured to implement the embodiments of present invention. The filter embodiments of the present invention can be a data processing algorithm that is executed by the microprocessor 122, described below. Light from light source 110 passes into patient tissue 112, and is scattered and detected by photodetector 114. A sensor 100 containing the light source and photodetector may also contain an encoder 116 which provides signals indicative of the wavelength of light source 110 to a detector/decoder 144 in a pulse oximeter 120 to allow the oximeter to select appropriate calibration coefficients for calculating oxygen saturation. Encoder 116 may, for instance, be a resistor.

Sensor 100 is connected to a pulse oximeter 120. The oximeter includes a microprocessor 122 connected to an internal bus 124. Also connected to the bus is a RAM memory 126 and a display 128. A time processing unit (TPU) 130 provides timing control signals to light drive circuitry 132 which controls when light source 110 is illuminated, and if multiple light sources are used, the multiplexed timing for the different light sources. TPU 130 also controls the gating-in of signals from photodetector 114 through an amplifier 133 and a switching circuit 134. These signals are sampled at the proper time, depending upon which of multiple light sources is illuminated, if multiple light sources are used. The received signal is passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier filter and A/D converters for multiple light wavelengths or spectrums received.

Based on the value of the received signals corresponding to the light received by photodetector 114, microprocessor 122 will calculate the oxygen saturation using various algorithms. These algorithms require coefficients, which may be empirically determined, corresponding to, for example, the wavelengths of light used. These are stored in a ROM 146. In a two-wavelength system, the particular set of coefficients chosen for any pair of wavelength spectrums is determined by the value indicated by encoder 116 corresponding to a particular light source in a particular sensor 100. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The brief description of an exemplary pulse oximeter set forth above, serves as a contextual fabric for describing the methods for reducing noise effects in the received signals according to embodiments of the present invention, which are described below. The embodiments of the present invention, which are used to reduce the noise effects in the signal using an assessment of the quality of the input signal, are described below in conjunction with the block diagram of FIG. 2.

A signal quality indicator is a measured parameter that is capable of estimating the reliability and accuracy of a signal. For example, when measuring blood oxygen saturation using a pulse oximeter, a signal quality indicator is able to indirectly assess whether an estimate of a value of blood oxygen saturation is an accurate one. This determination of accuracy is made possible by a thorough and detailed study of volumes of measured values and various indicators to determine which indicators are indicative of signal quality and what, if any, is the correlation between the indicator and the accuracy of the estimated value.

In pulse oximetry, examples of signal quality indicators include the skew of the time derivative of the signal; the correlation between signals from different wavelengths; the variation in signal amplitude, as well as others. Other assessments, such as maximum values or spectral peak frequencies, may also be used in determining filter parameters. In addition to these signal quality indicators, other signal quality indicators may also be used for the selection of filter coefficients. In pulse oximetry, these additional signal quality indicators include: a signal measure indicative of the degree of similarity of an infrared and red waveforms; a signal measure indicative of a low light level; a signal measure indicative of an arterial pulse shape; a signal measure indicative of the high frequency signal component in the measure value; a signal measure indicative of a consistency of a pulse shape; a signal measure indicative of an arterial pulse amplitude; a signal measure indicative of modulation ratios of red to infrared modulations and a signal measure indicative of a period of an arterial pulse. These various indicators provide for an indirect assessments of the presence of known error sources in pulse oximetry measurements, which include optical interference between the sensor and the tissue location; light modulation by other than the patient's pulsatile tissue bed; physical movement of the patient and improper tissue-to-sensor positioning. These additional signal quality indicators are described in further detail in a co-pending US patent application entitled: "SIGNAL QUALITY METRICS DESIGN FOR QUALIFYING DATA FOR A PHYSIOLOGICAL MONITOR," the disclosure of which is herein incorporated by reference in its entirety for all purposes.

Figure 2:
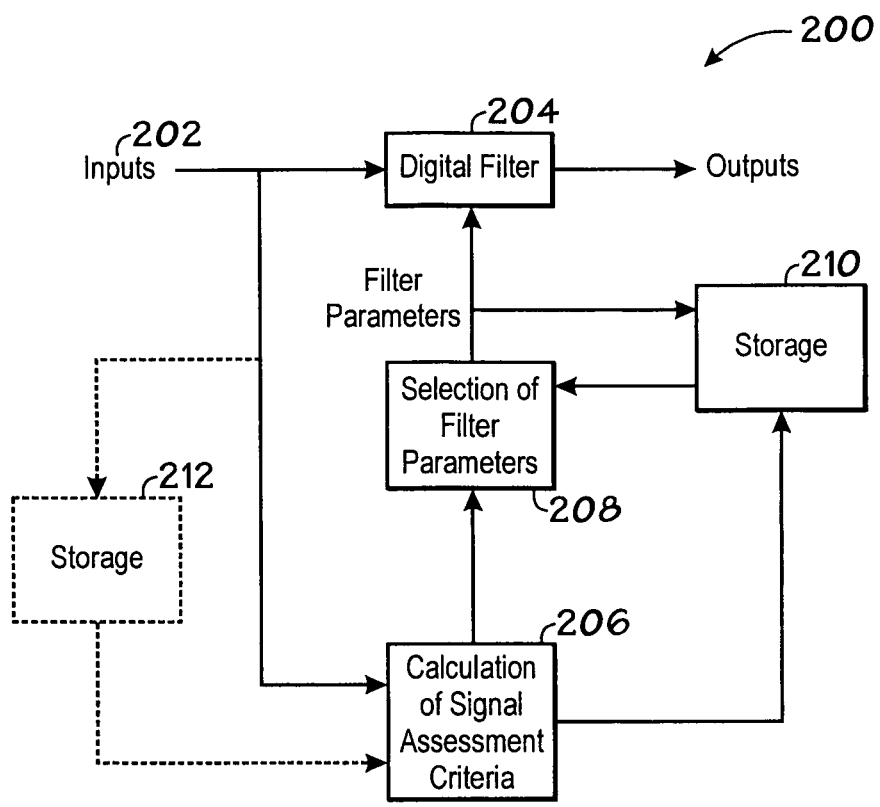
FIG. 2 is a block diagram depicting the operation of the signal-quality-based filter operation in accordance with embodiments of the present invention.

FIG. 2 is a block diagram 200 depicting the operation of the signal-quality-based selection of filter parameters in accordance with embodiments of the present invention. In one embodiment, the digital filter is a linear filter. For a linear filter is chosen, the filter can have either a finite or an infinite impulse response. Alternately, the filter may be a non-linear filter. Inputs 202 are applied to the digital filter 204 and to a signal quality assessment subsystem 206 that assesses how noisy the inputs look. Subsystem 206 calculates various signal quality metrics and provides the information to the selection subsystem 208, which selects filter parameters according to the criteria calculated by the signal quality subsystem 206. Storage subsystem 210 interfaces with the subsystems 206 and 208 to store and provide signal quality metrics as well as filter parameters. In one embodiment, the selection of filter parameters is performed in real time, with the filter parameters being determined using current input samples.

In an alternate embodiment, the filter parameters are calculated using a buffer 212 of recent input samples. In addition, signal assessment criteria and filter parameters can also be held in storage 210 for reference or for use in the calculation of new values.

As set forth above, various signal quality indicators may be used to select filter parameters. Additionally, the selection of the filter parameters may be based on more than one signal quality indicator. Furthermore, the selection of the filter parameters may be based on the output of an algorithm that combines several signal quality indicators. In one embodiment in an oximeter system, the variance in the raw saturation value is used to determine the filter's smoothing coefficients. In this embodiment, the selection is achieved by comparing the variance in the raw sat signal to several thresholds, and the filter's smoothing coefficients are selected depending on which range the variance falls in.

In an alternate embodiment in an oximeter system used for average pulse estimation, the filter parameter selection algorithm uses a combination of various signal quality metrics, Z to select values for filter coefficients for the digital filter, where $$Z = w_1 * SQ1 + w_2 * SQ2 + w_3 * SQ3,$$

where
  $w_1$, $w_2$, and $w_3$ are weighting factors
  SQ1 is a measure of the variance in the raw saturation signal
  SQ2 is a measure of the correlation between signals from different wavelengths
  SQ3 is a measure of the skew of the derivative waveform Yet alternately, instead of using Z to select the filter coefficients, a non-linear function of Z can be used to select a coefficient or coefficients for the filter. In operation, the selection algorithm may first be tuned before it is fully implemented in a particular diagnostics system. The tuning of the selection algorithm(s) may be done manually using heuristic approaches. Alternately, the selection algorithm may be tuned statistically, in a manner similar to training a neural network.

Embodiments of the present invention offer several advantages over conventional adaptive filtering. It is known that conventional adaptive filtering seeks to optimize some output criterion by continuously tuning the coefficients in a linear filter. The approach as embodied by the present invention is advantageous over conventional adaptive filtering for the following reasons. First, filter parameters in accordance with embodiments of the present invention are selected by switching among several preset or fixed values, rather than being varied or tuned continuously. By switching the parameters of the digital filter among fixed, preset values, the embodiments of the present invention provide for computational savings and simplicity of implementation. Second, the parameters of the digital filter are selected based upon an assessment of the input signal received by the filter rather than by comparing the filter's output with its input. This too, provides for computational savings and simplicity of implementation. Third, the filter need not be a linear filter, that is the filter is not required to be linear in its input-output relationship. Since the filter in accordance with embodiments of the present invention is not constrained to be linear, the filter's design can correspond more to physiological than to mathematical requirements, as is the case with most conventional adaptive filtering schemes. This physiological-based filter parameter selection may be used to, for example, attenuate pulse amplitudes above a threshold, or respond more quickly to decreases than to increases in blood oxygen saturation.

Accordingly, as will be understood by those of skill in the art, the present invention which is related to reducing noise effects in a system for measuring a physiological parameter, may be embodied in other specific forms without departing from the essential characteristics thereof. For example, signals indicative of any physiological parameter other than oxygen saturation, such as pulse rate, blood pressure, temperature, or any other physiological variable could be filtered using the techniques of the present invention. Moreover, many other indicators of the quality of the input signal can be used as a basis for the selection of the filter's coefficients. Further, while the present embodiments have been described in the time-domain, frequency-based methods are equally relevant to the embodiments of the present invention. Accordingly, the foregoing disclosure is intended to be illustrative, but not limiting, of the scope of the invention, which is set forth in the following claims.

The invention claimed is:

1. A method comprising:
  receiving a sequence of digital data inputs at a medical monitor;
  selecting one or more fixed digital filter coefficients for each digital data input based on at least one signal quality indicator for each respective digital data input, wherein the at least one signal quality indicator provides an estimate of accuracy of each respective digital data input; and
  filtering each digital data input using the respective one or more digital filter coefficients to generate respective filter outputs, wherein selecting one or more fixed digital filter coefficients comprises:
  accessing a data bank of stored coefficients.

2. The method, as set forth by claim 1, wherein filtering each digital data input comprises:
  configuring a linear digital filter using the respective one or more digital filter coefficients for each respective digital data input.

3. The method, as set forth by claim 1, wherein filtering each digital data input comprises:
  configuring a non-linear digital filter using the respective one or more digital filter coefficients for each respective digital data input.

4. The method, as set forth in claim 1, wherein the at least one signal quality indicator comprises at least one of a measure of variance in a raw saturation signal, a measure of correlation between signals from different wavelengths, a measure of skew of a derivative waveform of the data signal or a combination thereof.

5. A method comprising:
  receiving a sequence of digital data inputs at a medical monitor;
  selecting one or more fixed digital filter coefficients for each digital data input based on at least one signal quality indicator for each respective digital data input, wherein the at least one signal quality indicator provides an estimate of accuracy of each respective digital data input; and
  filtering each digital data input using the respective one or more digital filter coefficients to generate respective filter outputs, wherein selecting one or more fixed digital filter coefficients is not based on a comparison between each digital data input and the corresponding filter output.

6. The method, as set forth by claim 5, wherein filtering each digital data input comprises:
configuring a linear digital filter using the respective one or more digital filter coefficients for each respective digital data input.

7. The method, as set forth by claim 5, wherein filtering each digital data input comprises:
configuring a non-linear digital filter using the respective one or more digital filter coefficients for each respective digital data input.

8. The method, as set forth in claim 5, wherein the at least one signal quality indicator comprises at least one of a measure of variance in a raw saturation signal, a measure of correlation between signals from different wavelengths, a measure of skew of a derivative waveform of the data signal or a combination thereof.

9. A method comprising:
receiving a sequence of digital data inputs at a medical monitor;
obtaining at least one signal quality indicator for each digital data input, wherein the at least one signal quality indicator provides an estimate of accuracy of each respective digital data input;
selecting a fixed coefficient for a digital filter for each digital data input using the respective signal quality indicator, wherein selecting the fixed coefficient is performed without comparing an output signal from the digital filter with a corresponding digital data input; and
filtering the respective digital data input using the digital filter, wherein the at least one signal quality indicator comprises at least one of a measure of variance in a raw saturation signal, a measure of correlation between signals from different wavelengths, a measure of skew of a derivative waveform of the data signal or a combination thereof.

10. A method comprising:
receiving a sequence of digital data inputs at a medical monitor;
obtaining at least one signal quality indicator for each digital data input, wherein the at least one signal quality indicator provides an estimate of accuracy of each respective digital data input;
selecting a fixed coefficient for a digital filter for each digital data input using the respective signal quality indicator, wherein selecting the fixed coefficient is performed without comparing an output signal from the digital filter with a corresponding digital data input; and
filtering the respective digital data input using the digital filter, wherein selecting the fixed coefficients comprises:
selecting the fixed coefficients based on a non-linear function of the signal quality indicator.

11. A system, comprising:
a sensor adapted to deliver a data signal having a sequence of data inputs; and
a medical monitor comprising a digital filter configured to filter each respective data input using one of a plurality of fixed digital filter coefficients selected based on a respective signal quality indicator for each respective data input, wherein the at least one signal quality indicator provides an estimate of accuracy of each respective data input.

12. The system, as set forth by claim 11, wherein each digital filter coefficient is selected without comparing an output of the digital filter with a corresponding data input.

13. The system, as set forth by claim 11, wherein the digital filter is configured to filter each data input in substantially real time.

14. The system, as set forth by claim 11, wherein the digital filter comprises a linear filter.

15. The system, as set forth by claim 11, wherein the digital filter comprises a non-linear filter.

16. A system for reducing noise effects in pulse oximetry, comprising:
a pulse oximetry sensor adapted to acquire a sequence of digital data inputs;
a processor configured to obtain a respective preset filter coefficient for each respective digital data input of the sequence based on a determined noise level of each respective digital data input of the sequence; and
a digital filter configured to filter each respective digital data input using the respective preset filter coefficient.

17. The system, as set forth in claim 16, wherein the processor is configured to obtain the respective preset filter coefficient based upon at least one signal quality indicator of each respective digital data input, wherein the at least one signal quality indicator provides an estimate of accuracy of each respective digital data input.

18. The system, as set forth in claim 17, wherein the preset filter coefficients are derived using a non-linear function of the signal quality indicator.

19. A tangible non-transitory computer-readable medium comprising a computer program product, the computer program product comprising:
a first routine stored and executed on a medical monitor which, when executed, is capable of selecting one or more digital filter coefficients from a plurality of preset digital filter coefficients for each data input of a sequence using at least one signal quality indicator for each respective data input, wherein the at least one signal quality indicator provides an estimate of accuracy of each respective data input; and
a second routine stored and executed on a medical monitor which, when executed, is capable of filtering each data input using the respective one or more digital filter coefficients.

20. The tangible non-transitory computer-readable medium, as set forth in claim 19, wherein the first routine, when executed, is capable of selecting the one or more digital filter coefficients is configured to access a data bank.

21. The tangible non-transitory computer-readable medium, as set forth in claim 19, wherein the second routine, when executed, is capable of filtering each data input filters each data input in substantially real time.

22. The tangible non-transitory computer-readable medium, as set forth in claim 19, wherein the second routine, when executed, is capable of filtering each data input applies a linear filter.

23. The tangible non-transitory computer-readable medium, as set forth in claim 19, wherein the second routine, when executed, is capable of filtering each data input applies a non-linear filter.

24. A medical monitor comprising:
a memory storing a plurality of filter coefficients;
a processor configured to:
determine a signal quality indicator for each digital data input of an input signal received by the medical monitor, wherein the signal quality indicator provides an estimate of accuracy of each respective digital data input of the input signal;
select a filter coefficient from the plurality of filter coefficients based upon the signal quality indicator; and digitally filter each digital data input using the respective filter coefficient.

25. The medical monitor, as set forth in claim 24, wherein the processor comprises a digital filter configurable by each respective filter coefficient.

26. The medical monitor, as set forth in claim 24, wherein the signal quality indicator comprises at least one of a measure of variance in a raw saturation signal, a measure of correlation between signals from different wavelengths, a measure of skew of a derivative waveform of the signal, or a combination thereof.

27. The medical monitor, as set forth in claim 24, wherein the digital filter comprises a linear filter.

28. The medical monitor, as set forth in claim 24, wherein the digital filter comprises a non-linear filter.

* * * * *